US012758633B2

(12) United States Patent
Hu et al.

(10) Patent No.: US 12,758,633 B2
(45) Date of Patent: Oct. 13, 2026

(54) CARRIER FOR PROMOTING FENTON REACTION AND PREPARATION PROCESS AND USES THEREOF

(71) Applicant: National Tsing Hua University, Hsinchu (TW)

(72) Inventors: Shang-Hsiu Hu, Hsinchu (TW); Pin-Xuan Huang, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 325 days.

(21) Appl. No.: 18/380,674

(22) Filed: Oct. 17, 2023

(65) Prior Publication Data

US 2025/0099591 A1 Mar. 27, 2025

(30) Foreign Application Priority Data

Sep. 22, 2023 (TW) ................................ 112136252

(51) Int. Cl.

| | |
|---|---|
| ***A61K 41/00*** | (2020.01) |
| ***A61K 31/713*** | (2006.01) |
| ***A61K 47/69*** | (2017.01) |
| ***A61P 35/00*** | (2006.01) |
| ***C12N 15/113*** | (2010.01) |

(52) U.S. Cl.

CPC ........ *A61K 41/0057* (2013.01); *A61K 31/713* (2013.01); *A61K 47/6923* (2017.08); *A61P 35/00* (2018.01); *C12N 15/1138* (2013.01); *C12N 2310/14* (2013.01)

(58) Field of Classification Search

None

See application file for complete search history.

(56) References Cited

U.S. PATENT DOCUMENTS

| | | | | |
|---|---|---|---|---|
| 2015/0246137 A1* | 9/2015 | Guo | ........................ | A61K 9/127<br>424/649 |
| 2020/0163899 A1* | 5/2020 | Fernandes | ............... | A61P 43/00 |

OTHER PUBLICATIONS

Zhao, Journal of Pharmaceutical Sciences, 2007 (Year: 2007).*

* cited by examiner

*Primary Examiner* — Susan T Tran
*Assistant Examiner* — William Craigo
(74) *Attorney, Agent, or Firm* — WPAT, PC

(57) ABSTRACT

The present disclosure provides a carrier for promoting Fenton reaction and the preparation process and uses thereof. The carrier for promoting Fenton reaction of the present disclosure achieves the effect of enhancing gene delivery efficiency and gene therapy for cancer through various efficacy experiments.

18 Claims, 8 Drawing Sheets

CARRIER FOR PROMOTING FENTON REACTION AND PREPARATION PROCESS AND USES THEREOF

CROSS-REFERENCE TO RELATED APPLICATION

This application claims priority of Taiwan patent application No. 112136252, filed on Sep. 22, 2023, the content of which is incorporated herein in its entirety by reference.

BACKGROUND OF THE INVENTION

1. Field of the Invention

The present invention relates to a carrier for promoting Fenton reaction and the preparation process and uses thereof.

2. The Prior Art

In recent years, gene therapy has been considered as a potential disease treatment method. There are two methods of gene delivery: viral and non-viral. Viral vectors are used for gene delivery due to their high transfection efficiency, but their clinical application is limited due to the toxicity and immunogenicity of viral vectors. Therefore, many non-viral forms of gene delivery have been studied to solve their limitations. However, most of these vectors face the problem of low transfection efficiency. Therefore, it is desirable to develop gene delivery carriers that can improve transfection efficiency.

In order to solve the above-mentioned problems, those skilled in the art urgently need to develop a novel carrier for enhancing gene delivery efficiency and the preparation process and uses thereof for the benefit of a large group of people in need thereof.

SUMMARY OF THE INVENTION

A primary objective of the present invention is to provide a carrier for promoting Fenton reaction, comprising a Prussian blue nanocube and a lipid component.

According to an embodiment of the present invention, the lipid component coats the Prussian blue nanocube.

According to an embodiment of the present invention, the lipid component comprises 1,2-dioleoyl-3-trimethylammonium-propane (DOTAP), methoxy-polyethylene-aldehyde (mPEG-CHO) and cholesterol.

According to an embodiment of the present invention, the DOTAP is a cationic lipid component.

According to an embodiment of the present invention, a molar ratio of the DOTAP, the mPEG-CHO and the cholesterol is 5:1:4.

According to an embodiment of the present invention, a ratio of the mPEG-CHO to the carrier is 5-40 wt %.

According to an embodiment of the present invention, a ratio of the DOTAP to the carrier is 30-50 wt %.

According to an embodiment of the present invention, a ratio of the cholesterol to the carrier is 20-35 wt %.

According to an embodiment of the present invention, a ratio of the Prussian blue nanocube to the carrier is 1-10 wt %.

Another objective of the present invention is to provide a method for preparing the carrier according to claim 1, comprising the following steps: (a) dissolving polyvinylpyrrolidone (PVP) and potassium hexacyanoferrate (III) ($K_3[Fe(CN)_6]$) in deionized water to obtain a yellow solution; (b) adding hydrochloric acid to the yellow solution, stirring at room temperature, followed by heating to obtain a blue solution; (c) performing centrifugation to the blue solution and washing with alcohol to collect precipitate, resuspending the precipitate in the alcohol, followed by drying to obtain the Prussian blue nanocube; and (d) dissolving the lipid component in the alcohol, adding the Prussian blue nanocube and evaporating the alcohol to obtain the carrier.

According to an embodiment of the present invention, in step (d), after the alcohol is evaporated, a thin lipid film is formed, phosphate buffered saline (PBS) is added, and the thin lipid film is subjected to ultrasonic hydration treatment.

Another objective of the present invention is to provide a method for enhancing gene delivery efficiency, comprising administering to a subject in need thereof a composition comprising an effective amount of the aforementioned carrier.

Another objective of the present invention is to provide a method for gene therapy of cancer, comprising administering to a subject in need thereof a pharmaceutical composition comprising an effective amount of the aforementioned carrier.

According to an embodiment of the present invention, the cancer is lung cancer.

Another objective of the present invention is to provide a method for targeting lung, comprising administering to a subject in need thereof a composition comprising an effective amount of the aforementioned carrier.

In summary, the carrier for promoting Fenton reaction of the present invention has the following effect. The structure of the cationic lipid is similar to that of the natural lipid, and the positively charged polar base head can be combined with the nucleic acid to stabilize the nucleic acid, and can increase the ability of the nucleic acid to be degraded. In addition, adding the Prussian blue nanocube to the lipid component can increase the efficiency of gene transfection and delivery by virtue of its ability to generate Fenton reaction, and has the potential to treat cancer by gene therapy.

BRIEF DESCRIPTION OF THE DRAWINGS

The following drawings form part of the present specification and are included here to further demonstrate some aspects of the present invention, which can be better understood by reference to one or more of these drawings, in combination with the detailed description of the embodiments presented herein.

(FIG. 1A) (a1) Prussian blue nanocube (PB); (a2) PB@lipid particle (LP); (b1) Transmission electron microscope (TEM) images of iron oxide nanoparticles (IO) and (b2) lipid-modified iron oxide (IO@LP). (FIG. 1B) Size distribution and zeta potential of PB, PB@LP, IO, IO@LP and 1,2-dioleoyl-3-trimethylammonium-propane (DOTAP). The DOTAP group contains DOTAP, mPEG-CHO and cholesterol, which is LP without PB or IO coating.

FIGS. 2A-2D show that the PB of PB@LP of the present invention generates reactive oxygen species (ROS) through the Fenton reaction, in which FIG. 2A is a schematic diagram of the ·OH catalytic process of the PB of PB@LP. FIG. 2B shows the UV-visible absorption spectrum of oxidation o-phenylenediamine (ox OPD) after Fenton reaction with different concentrations of PB of PB@LP. FIG. 2C shows the UV-visible absorption spectrum and images (FIG.

2D) of oxidation o-phenylenediamine (ox OPD) after adding (1) PBS; (2) PBS+$H_2O_2$; (3) $Fe_2O_3$+$H_2O_2$; (4) PB+$H_2O_2$.

Figure 3A:
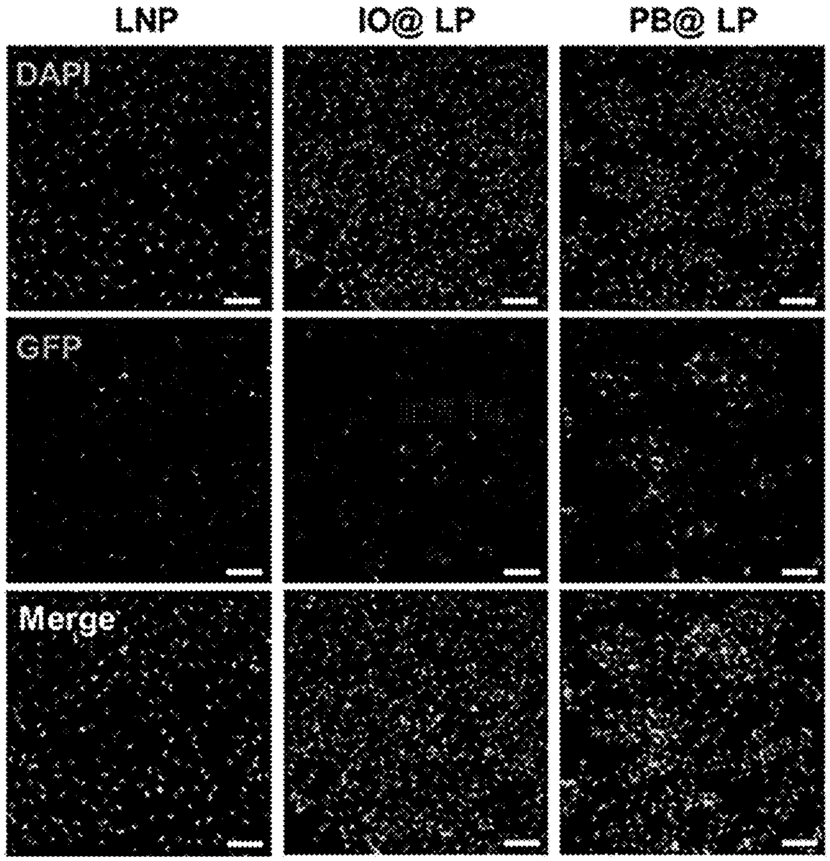
Figure 3B:
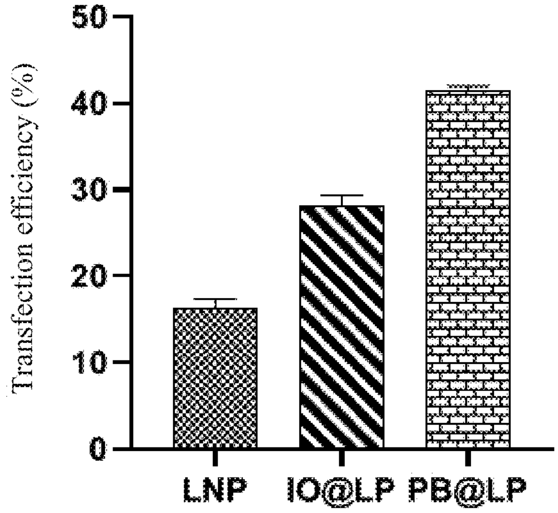

FIGS. 3A and 3B show the confocal laser scanning microscope (CLSM) images of green fluorescent protein (GFP) expression after different lipid-modified carriers were cultured with mouse skin melanoma B16F10 cells for 48 hours. 4',6-diamidino-2-phenylindole (DAPI) represents nuclei; GFP represents cells with green fluorescent protein. Scale bar: 100 μm; LNP means the comparison group without coating PB or IO.

Figure 4A:
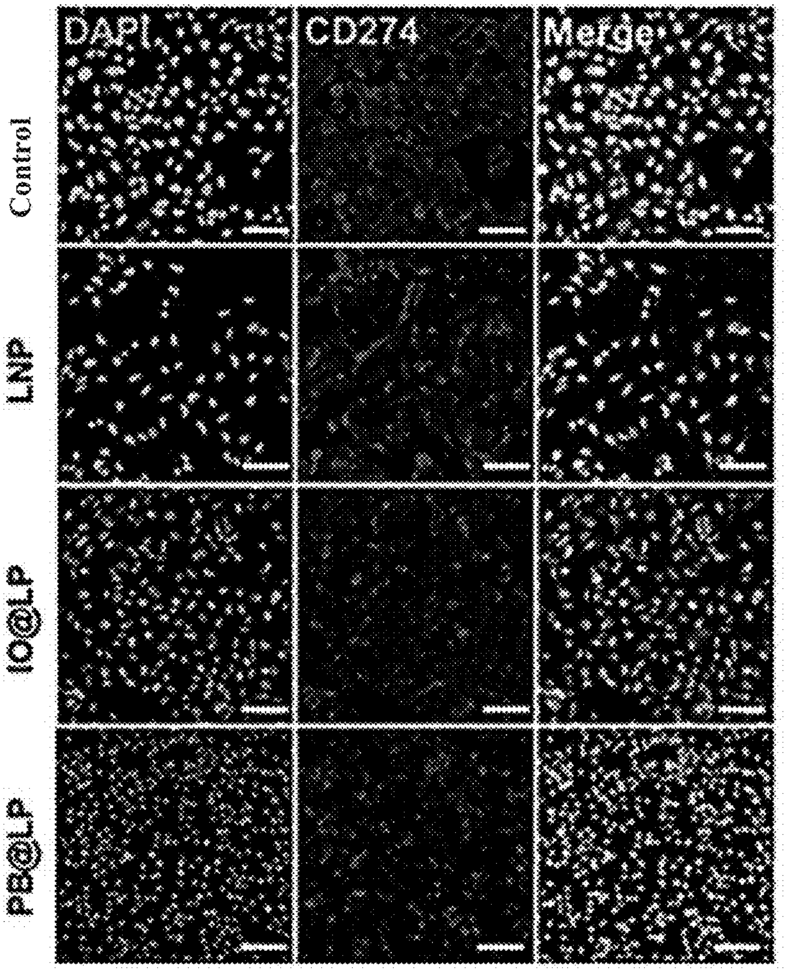
Figure 4B:
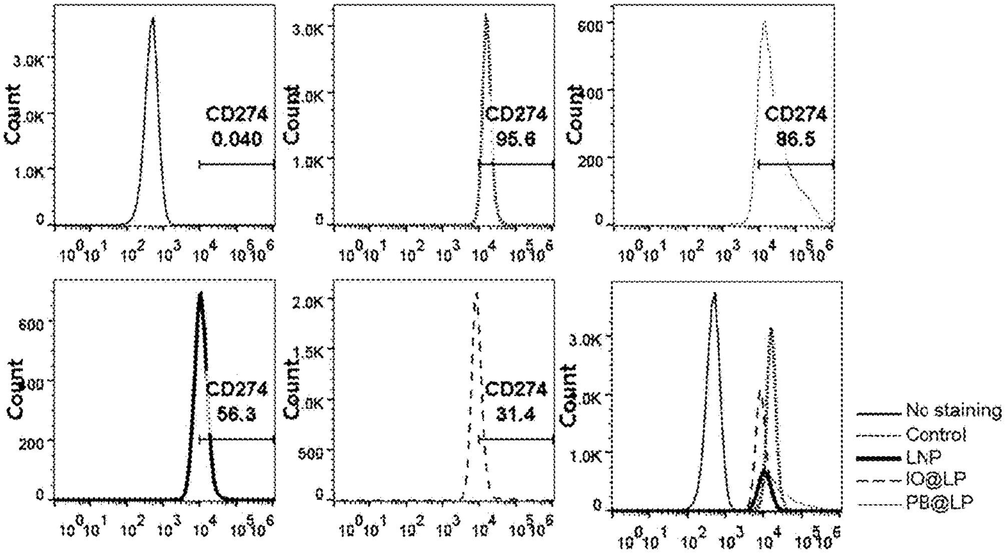

FIGS. 4A and 4B show that different lipid-modified carriers loaded with programmed cell death 1 ligand 1 (PD-L1) siRNA were cultured with mouse skin melanoma B16F10 cells for 48 hours, and (4A) Confocal microscopic images and (4B) Flow cytometry were used to detect PD-L1 protein expression on B16F10 cells. Blue represents DAPI stained nuclei; Purple represents the expression of PD-L1. Scale bar: 60 μm; LNP means the comparison group.

Figure 5:
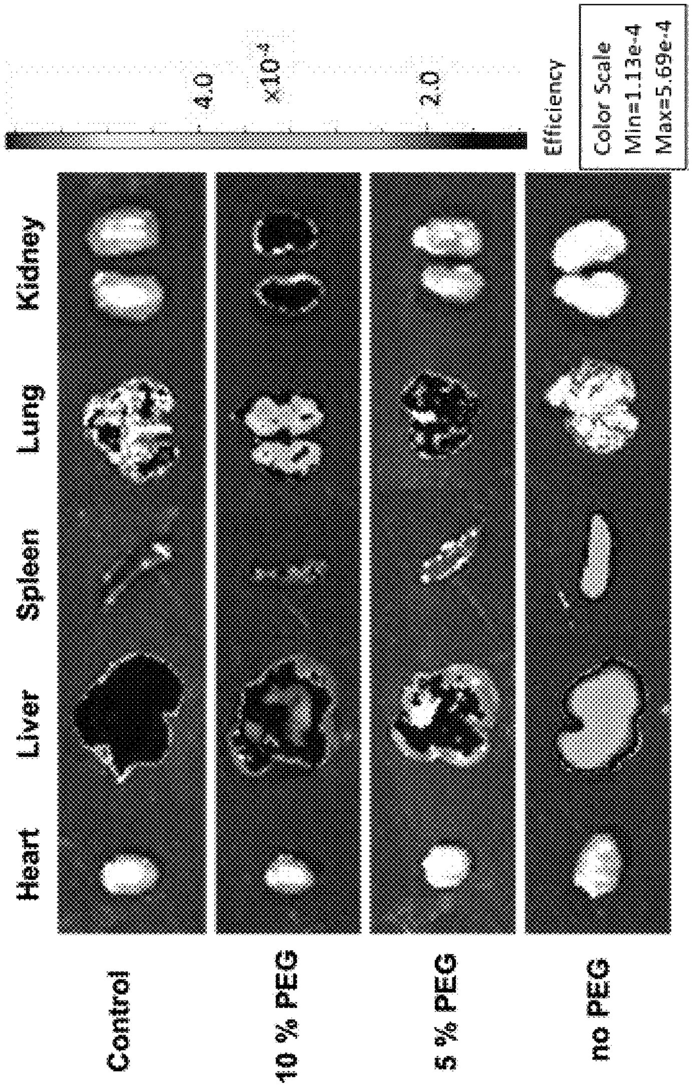

FIG. 5 shows the use of a non-invasive 3D in vivo molecular imaging system (IVIS) to detect the accumulation of lipid-modified carrier PB@LP with different proportions of polyethylene glycol (PEG) in the lungs.

Figure 6:
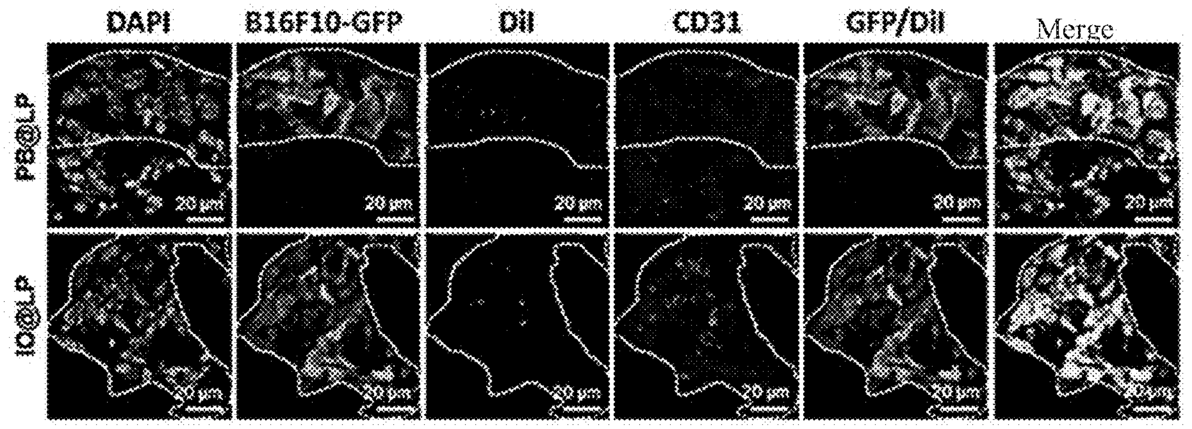

FIG. 6 shows fluorescent staining CLSM images of the carrier entering the tumor after injecting PB@LP and IO@LP through the tail vein in an animal model having lung tumor metastasis. DAPI represents nuclei; B16F10-GFP represents B16F10 cells with green fluorescent protein; DiI represents lipid carriers labeled with DiI (a cyan dye used in cell biology); CD31 represents vascular endothelial cells. Scale bar: 20 μm.

Figure 7:
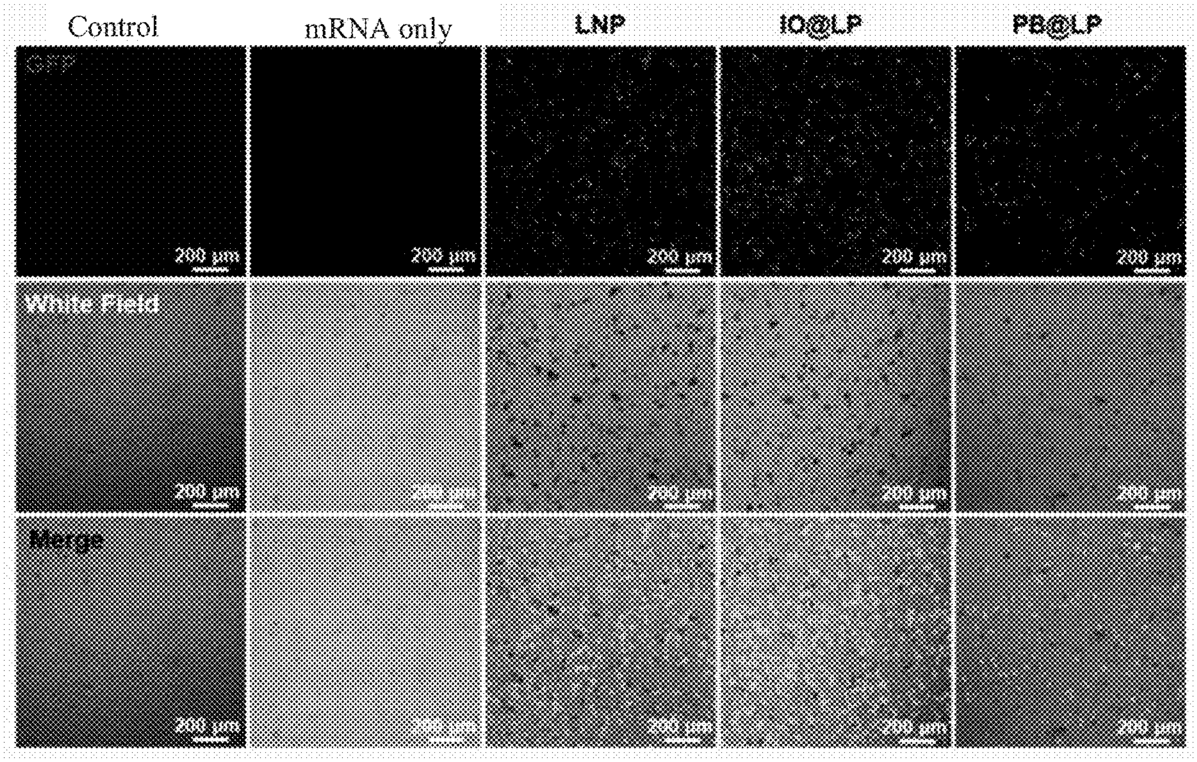

FIG. 7 shows that GFP mRNA was loaded onto different lipid-modified carriers and cultured with mouse skin melanoma B16F10 cells for 24 hours to observe the expression of green fluorescent protein (GFP). LNP means the comparison group.

DETAILED DESCRIPTION OF THE PREFERRED EMBODIMENT

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

As used herein, the data provided represent experimental values that can vary within a range of ±20%, preferably within ±10%, and most preferably within ±5%.

Unless otherwise stated in the context, "a", "the" and similar terms used in the specification (especially in the following claims) should be understood as including singular and plural forms.

According to the present invention, the term "Fenton reaction" is an inorganic chemical reaction. The process is that a mixed solution of hydrogen peroxide ($H_2O_2$) and ferrous iron ions $Fe^{2+}$ oxidizes many known organic compounds such as carboxylic acids, alcohols, and esters into inorganic states. Cancer cells are dead by producing reactive oxygen species (ROS) through the Fenton reaction.

According to the present invention, the chemical name of the term "Prussian blue" is iron ferrocyanide; molecular formula: $Fe_7(CN)_{18}\cdot14H_2O$, which is a dark blue pigment.

According to the present invention, the term "1,2-dioleoyl-3-trimethylammonium-propane (DOTAP)" is a cationic lipid.

According to the present invention, the molecular formula of the term "methoxy-polyethylene-aldehyde (mPEG-CHO)" is $CH_3O(CH_2CH_2O)_nCH_2$—$CONHCH_2CH_2CHO$, which needs to be stored under dry conditions at −20° C. and protected by inert gas.

According to the present invention, the pharmaceutical composition can be manufactured to a dosage form suitable for parenteral or oral administration, using techniques well known to those skilled in the art, including, but not limited to, injection (e.g., sterile aqueous solution or dispersion), sterile powder, tablet, troche, lozenge, pill, capsule, dispersible powder or granule, solution, suspension, emulsion, syrup, elixir, slurry, and the like.

The pharmaceutical composition according to the present invention may be administered by a parenteral route selected from the group consisting of: intraperitoneal injection, subcutaneous injection, intraepidermal injection, intradermal injection, intramuscular injection, intravenous injection, intralesional injection, sublingual administration, and transdermal administration.

The pharmaceutical composition according to the present invention can comprise a pharmaceutically acceptable carrier which is widely used in pharmaceutical manufacturing technology. For example, the pharmaceutically acceptable carrier can comprise one or more reagents selected from the group consisting of solvent, emulsifier, suspending agent, decomposer, binding agent, excipient, stabilizing agent, chelating agent, diluent, gelling agent, preservative, lubricant, absorption delaying agent, liposome, and the like. The selection and quantity of these reagents fall within the scope of the professional literacy and routine techniques of those skilled in the art.

According to the present invention, the pharmaceutically acceptable carrier comprises a solvent selected from the group consisting of water, normal saline, phosphate buffered saline (PBS), sugar solution, aqueous solution containing alcohol, and combinations thereof.

Example 1

Preparation of Prussian Blue Nanocube and Iron Oxide Nanoparticles (IO)

3 g of polyvinylpyrrolidone (PVP) (N-vinyl-2-pyrrolidone polymerized compound) (K30) and 226.7 mg of potassium hexacyanoferrate (III) ($K_3[Fe(CN)_6]$) were dissolved in 40 mL of deionized water. Under vigorous magnetic stirring, a clear yellow solution was formed. 35 μL of concentrated hydrochloric acid (HCl, 12 M) was added and stirred at room temperature for 30 minutes, and the solution was placed in an 85° C. oven for 20 hours to obtain a dark blue Prussian blue nanocube solution. The solution was centrifuged (12,000 rpm, 10 min) and washed 3 times with 75% ethanol to collect the precipitate. The precipitate was resuspended in 3-5 mL of 75% ethanol and dried overnight at 60° C. to obtain single crystals of Prussian blue nanocubes. The iron oxide in the comparison group is commercial iron oxide with a size of about 5 nanometers, and the surface modification was performed with polyethylene.

Example 2

Preparation of Carrier for Promoting Fenton Reaction (Lipid-Modified Prussian Blue Nanocube, Referred to as PB@LP) and Lipid-Modified Iron Oxide (IO@LP)

In order to obtain PB@LP, the lipid component (including 1,2-dioleoyl-3-trimethylammonium-propane (DOTAP), methoxy methoxy-polyethylene-aldehyde (mPEG-CHO) and cholesterol) (molar ratio 5:1:4) were dissolved in ethanol. 1-10% Prussian blue nanocubes or iron oxide (IO) were added to the solution and ethanol was evaporated at room temperature to form a thin lipid film. Phosphate buffered saline (PBS) was added at pH 7.4, and the lipid film was hydrated through ultrasound to obtain 5 mM PB@LP. The prepared PB@LP was centrifuged at 12,000 rpm for 10 minutes to remove the carrier without Prussian blue nanocubes. In the present invention, the mPEG-CHO ratio is greatly increased to 5-40 wt %, which is different from the 1-2% ratio in the prior art. In addition, the use of mPEG-CHO can effectively provide tumor penetration effect. The ratio of mPEG-CHO can also be adjusted from 5 wt % to 40 wt %, all of which have corresponding gene delivery effects.

Table 1 shows the ratios of each component in PB@LP and IO@LP.

TABLE 1

| | DOTAP (wt %) | mPEG-CHO (wt %) | Cholesterol (wt %) | Prussian blue nanocube (wt %) | Iron oxide (wt %) |
|---|---|---|---|---|---|
| 1 | 50 | 20 | 29 | / | 1 |
| 2 | 50 | 20 | 29 | 1 | |
| 3 | 50 | 10 | 35 | / | 5 |
| 4 | 50 | 10 | 35 | 5 | / |
| 5 | 50 | 5 | 35 | / | 10 |
| 6 | 50 | 5 | 35 | 10 | / |
| 7 | 40 | 30 | 25 | / | 5 |
| 8 | 40 | 30 | 25 | 5 | / |
| 9 | 30 | 40 | 20 | / | 10 |
| 10 | 30 | 40 | 20 | 10 | / |

Figure 1A:
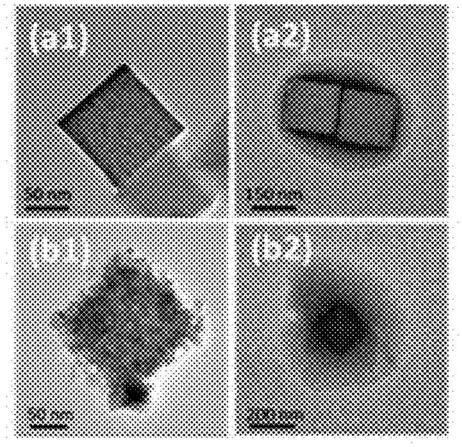
FIGS. 1A and 1B show the characterization of the carrier that promotes the Fenton reaction (PB@LP).
Figure 1B:
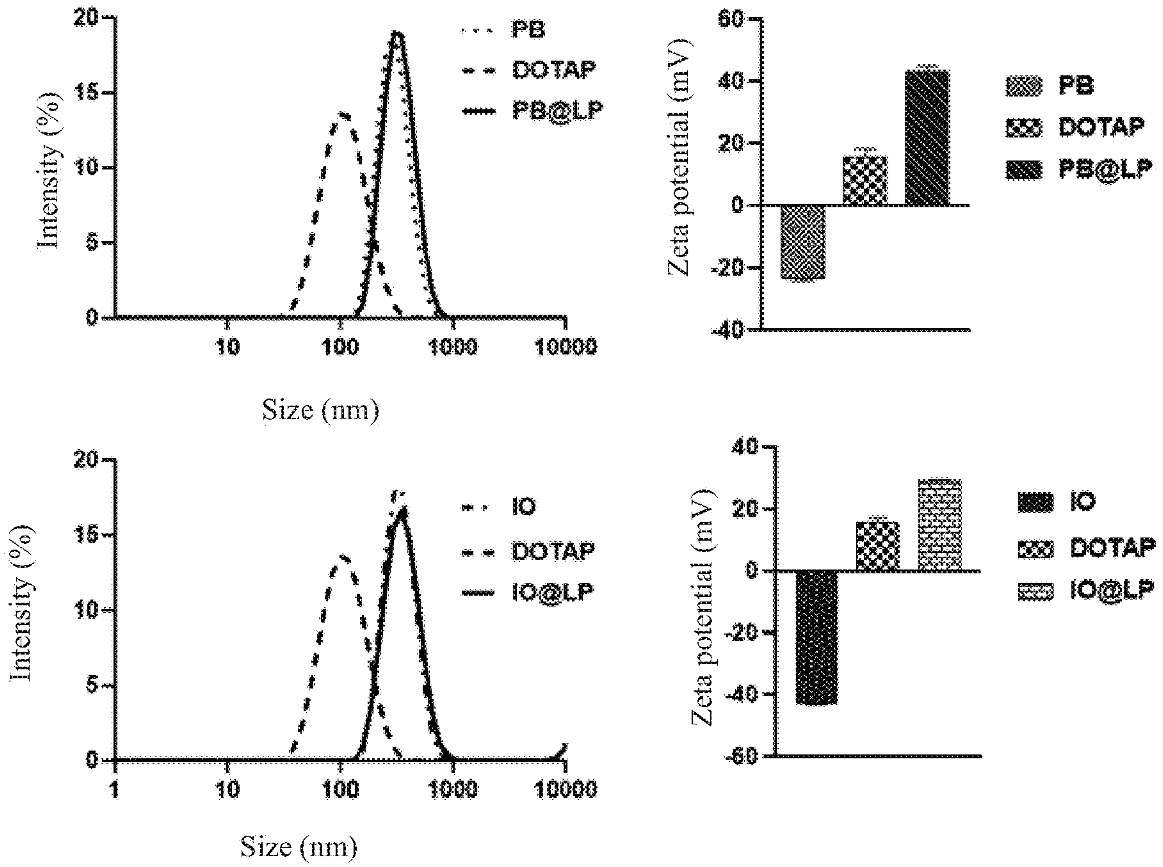

FIGS. 1A and 1B show the characterization of the carrier that promotes the Fenton reaction (PB@LP). (FIG. 1A) (a1) Prussian blue nanocube (PB); (a2) PB@lipid particle (LP); (b1) Transmission electron microscope (TEM) images of iron oxide nanoparticles (IO) and (b2) lipid-modified iron oxide (IO@LP). (FIG. 1B) Size distribution and zeta potential of PB, PB@LP, IO, IO@LP and 1,2-dioleoyl-3-trimethylammonium-propane (DOTAP). The DOTAP group contains DOTAP, mPEG-CHO and cholesterol, which is LP without PB or IO coating.

In order to confirm whether the Prussian blue nanocubes coated with cationic lipids (including DOTAP, mPEG-CHO and cholesterol) and iron oxide nanoparticles were successfully synthesized, a transmission electron microscope (TEM) and dynamic light scattering (DLS) were used to detect particle formation. TEM image results show that the Prussian blue nanocube morphology is cubic, the $Fe_2O_3$ morphology is rough, while the PB@LP and IO@LP morphology are round, and their tetragonal structure can be seen (FIG. 1A). In addition, DLS shows that the original size of cationic lipid nanoparticles is about 100 nanometers, and the size after coating with Prussian blue nanocubes or $Fe_2O_3$ is about 500 nanometers. The surface charge of Prussian blue nanocubes and $Fe_2O_3$ was originally negative, but after coating with cationic lipids, the surface charge became positive (FIG. 1B). From the above results, it can be seen that PB@LP and IO@LP were successfully synthesized.

Example 3

Evaluation of Ability of PB in PB@LP to Generate Reactive Oxygen Species (ROS)

Figure 2A:
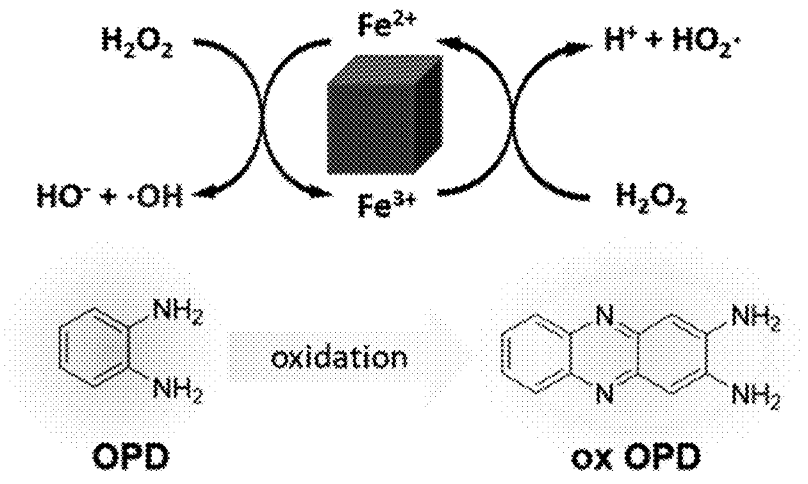
Figure 2B:
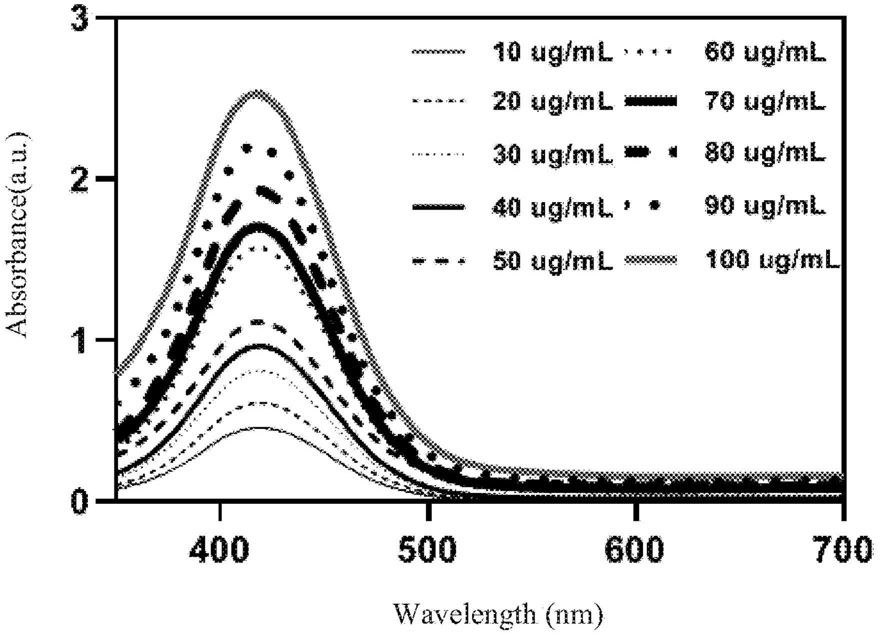
Figure 2C:
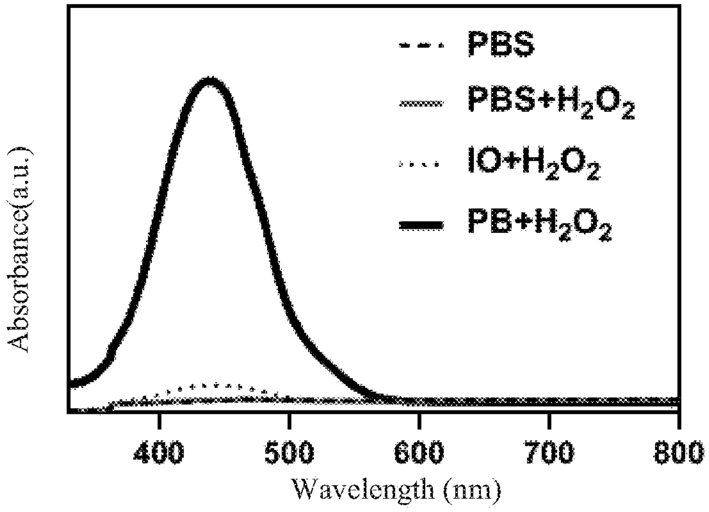

FIGS. 2A-2D show that the PB of PB@LP of the present invention generates reactive oxygen species (ROS) through the Fenton reaction, in which FIG. 2A is a schematic diagram of the ·OH catalytic process of the PB of PB@LP. FIG. 2B shows the UV-visible absorption spectrum of oxidation o-phenylenediamine (ox OPD) after Fenton reaction with different concentrations of PB of PB@LP. FIG. 2C shows the UV-visible absorption spectrum and images (FIG. 2D) of oxidation o-phenylenediamine (ox OPD) after adding (1) PBS; (2) PBS+$H_2O_2$; (3) $Fe_2O_3$+$H_2O_2$; (4) PB+$H_2O_2$.

Figure 2D:
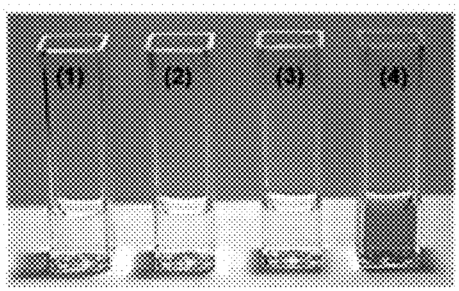

The hydroxyl radicals (·OH) generated by the Fenton reaction of PB in PB@LP catalyzing hydrogen peroxide ($H_2O_2$) would oxidize the colorless o-phosphophenylenediamine (OPD) into a yellow dimer (FIG. 2A). The ability of PB in PB@LP to produce reactive oxygen species (ROS) was evaluated by detecting the production of this dimer by ultraviolet-visible spectroscopy (UV-Vis). In this part of the experiment, different concentrations of PB in PB@LP were added to 0.5 mM OPD and 2.5 mM $H_2O_2$. After waiting for 20 minutes, UV-Vis was used to measure the absorption value at 417 nm. It can be seen that when the PB concentration in PB@LP is higher, the absorption value is higher, indicating that the PB in PB@LP can generate ROS through Fenton reaction (FIG. 2B). In addition, in order to compare the ability of PB@LP to generate ROS through Fenton reaction, iron oxide nanoparticles containing iron were used for comparison. The results show that compared to iron oxide nanoparticles, PB in PB@LP has a better ability to generate ROS (FIGS. 2C and 2D).

Example 4

Evaluation of Effect of PB@LP on Gene Delivery

In order to evaluate the effect of gene delivery, plasmid DNA (pDNA) with gene encoding green fluorescent protein (GFP) was loaded into PB@LP. Mouse skin melanoma B16F10 cells (BCRC60031) were seeded in a 24-well culture plate at a density of $2.5\times10^4$ cells per well. After cell attachment, cells were cultured with PB@LP loaded with pDNA-GFP at a concentration of 10 μg/mL in serum-free medium. After 6 hours, 10% fetal bovine serum (FBS) medium was added to each well to maintain cell growth for 48 hours. The expression of GFP after transfection was examined through confocal laser scanning microscope (CLSM).

FIG. 3A shows the confocal laser scanning microscope (CLSM) images of green fluorescent protein (GFP) expression after different lipid-modified carriers were cultured with mouse skin melanoma B16F10 cells for 48 hours. 4',6-diamidino-2-phenylindole (DAPI) represents nuclei; GFP represents cells with green fluorescent protein. Scale bar: 100 μm; LNP means the comparison group without coating PB or IO.

As shown in FIG. 3B, the transfection efficiency of the group with only cationic lipids is about 16%, IO@LP is about 28%, and the transfection efficiency of PB@LP is about 41%. The results show that compared with IO@LP coated with iron elements, the transfection efficiency of carrier PB@LP, which can generate more ROS, is 13% higher (FIG. 3).

Example 5

Evaluation of Effect of PB@LP on Inhibiting Protein Expression of Programmed Cell Death 1 Ligand 1 (PD-L1) in Cancer Cells If PD-L1 siRNA effectively enters cells and exerts its effects, the PD-L1 protein on the surface of cancer cells would be reduced. In order to evaluate the effect of siRNA delivery, PD-L1 siRNA was first loaded into PB@LP, and then added to the cell culture medium and cultured with B16F10 cells for 48 hours. Finally, immunohistochemical staining and flow cytometry were used to detect the expression level of PD-L1.

FIGS. 4A and 4B show that different lipid-modified carriers loaded with programmed cell death 1 ligand 1 (PD-L1) siRNA were cultured with mouse skin melanoma B16F10 cells for 48 hours, and (4A) Confocal microscopic images and (4B) Flow cytometry were used to detect PD-L1 protein expression on B16F10 cells. Blue represents DAPI stained nuclei; Purple represents the expression of PD-L1. Scale bar: 60 μm; LNP means the comparison group.

As shown in FIGS. 4A and 4B, the PD-L1 expression level of the lipid carrier loaded with PD-L1 siRNA was lower than that of the control group. According to the results of flow cytometry, compared with the control group, the expression level of PD-L1 in the LNP group was reduced by nearly 40%, while the expression level of PD-L1 in the IO@LP group was reduced by 64.2%. However, there was almost no decrease in the PB@LP group (FIG. 4B). It is shown that this lipid carrier PB@LP loaded with PD-L1 siRNA can effectively inhibit the expression of PD-L1 protein on cancer cells and may be able to increase the activity of T cells in immunotherapy in the future.

Example 6

Evaluation of Effect of PB@LP on Gene Therapy of Cancers In Vivo

In order to evaluate whether the PB@LP lipid carrier can successfully stay in the lungs to facilitate subsequent treatment of metastasis of lung cancer. In animal models of metastasis of lung cancer, lipid carriers stained with DiI (a cyan dye used in cell biology) were injected through the tail vein to observe whether the lipid carriers could enter the lungs. On day 0, B16F10 melanoma cells with GFP were injected into C57BL/6 mice through the tail vein at a concentration of $5\times10^6$ cells/mL. On day 13, 100 μL of lipid carrier at a concentration of 5 mM was injected, and the mice were sacrificed by perfusion 24 hours later. After removing major organs such as the mouse's heart, liver, spleen, lungs, and kidneys, the non-invasive 3D in vivo molecular imaging system (IVIS) was performed.

FIG. 5 shows the use of a non-invasive 3D in vivo molecular imaging system (IVIS) to detect the accumulation of lipid-modified carrier PB@LP with different proportions of polyethylene glycol (PEG) in the lungs. The results show that using the lipid-modified carrier PB@LP increases the transfection rate by 50-80%. As the concentration of PEG increases, the accumulation in the lungs also increases (FIG. 5), while no significant accumulation is seen in cancers in other organs.

Example 7

Evaluation of Effect of PB@LP on In Vivo Cancer Gene Therapy

In order to evaluate whether the PB@LP lipid carrier can be used for subsequent cancer gene therapy in vivo, in animal models of metastasis of lung cancer, DiI-stained PB@LP and IO@LP were injected through the tail vein to observe whether PB@LP and IO@LP could enter the tumor. On day 0, B16F10 melanoma cells with GFP were injected into C57BL/6 mice through the tail vein at a concentration of $1\times10^6$ cells/mL. On day 13, 100 μL of lipid carrier at a concentration of 5 mM was injected, and the mice were sacrificed by perfusion 24 hours later. The mouse lungs were cryosectioned and immunohistochemical staining was performed to observe the accumulation of PB@LP and IO@LP in the lungs using confocal microscopy.

FIG. 6 shows fluorescent staining CLSM images of the carrier entering the tumor after injecting PB@LP and IO@LP through the tail vein in an animal model having lung tumor metastasis. DAPI represents nuclei; B16F10-GFP represents B16F10 cells with green fluorescent protein; DiI represents lipid carriers labeled with DiI (a cyan dye used in cell biology); CD31 represents vascular endothelial cells. Scale bar: 20 μm.

As shown in FIG. 6, there is accumulation of DiI-labeled PB@LP and IO@LP in the tumor area with green fluorescence. It can be seen that PB@LP can enter the tumor through blood circulation and would be beneficial to subsequent gene delivery treatments in the future (FIG. 6).

Example 8

PB@LP Applied to Other Gene Delivery Systems

In order to test whether the lipid carrier can be applied to other gene delivery systems, this example uses GFP mRNA to be loaded onto the lipid carrier and cultured with B16F10 cells for 24 hours to express green fluorescent protein.

FIG. 7 shows that GFP mRNA was loaded onto different lipid-modified carriers and cultured with mouse skin melanoma B16F10 cells for 24 hours to observe the expression of green fluorescent protein (GFP). LNP means the comparison group. The results show that the lipid carrier can effectively deliver mRNA into cells and express the corresponding protein. Therefore, PB@LP can effectively deliver mRNA (FIG. 7).

In summary, the carrier for promoting Fenton reaction of the present invention has the following effect. The structure of the cationic lipid is similar to that of the natural lipid, and the positively charged polar base head can be combined with the nucleic acid to stabilize the nucleic acid, and can increase the ability of the nucleic acid to be degraded. In addition, adding the Prussian blue nanocube to the lipid component can increase the efficiency of gene transfection and delivery by virtue of its ability to generate Fenton reaction, and has the potential to treat cancer by gene therapy.

Although the present invention has been described with reference to the preferred embodiments, it will be apparent to those skilled in the art that a variety of modifications and changes in form and detail may be made without departing from the scope of the present invention defined by the appended claims.

What is claimed is:

1. A carrier for promoting Fenton reaction, comprising a Prussian blue nanocube and a lipid component, wherein the lipid component comprises 1,2-dioleoyl-3-trimethylammonium-propane (DOTAP), aldehyde (CHO) functionalized methoxy polyethylene glycol (mPEG-aldehyde) and cholesterol, wherein a ratio of the cholesterol to the carrier is 20-35 wt %.

2. The carrier according to claim 1, wherein the lipid component coats the Prussian blue nanocube.

3. The carrier according to claim 1, wherein the DOTAP is a cationic lipid component.

4. The carrier according to claim 3, wherein a molar ratio of the DOTAP, the mPEG-aldehyde and the cholesterol is 5:1:4.

5. The carrier according to claim 3, wherein a ratio of the mPEG-aldehyde to the carrier is 5-40 wt %.

6. The carrier according to claim 3, wherein a ratio of the DOTAP to the carrier is 30-50 wt %.

7. The carrier according to claim 1, wherein a ratio of the Prussian blue nanocube to the carrier is 1-10 wt %.

8. A method for preparing the carrier according to claim 1, comprising the following steps:

(a) dissolving polyvinylpyrrolidone (PVP) and potassium hexacyanoferrate (III) (K3[Fe(CN)6]) in deionized water to obtain a yellow solution;

(b) adding hydrochloric acid to the yellow solution, stirring at room temperature, followed by heating to obtain a blue solution;

(c) performing centrifugation to the blue solution and washing with alcohol to collect precipitate, resuspending the precipitate in the alcohol, followed by drying to obtain the Prussian blue nanocube; and (d) dissolving the lipid component in the alcohol, adding the Prussian blue nanocube and evaporating the alcohol to obtain the carrier.

9. The method according to claim 8, wherein in step (d), after the alcohol is evaporated, a thin lipid film is formed, phosphate buffered saline (PBS) is added, and the thin lipid film is subjected to ultrasonic hydration treatment.

10. The method according to claim 8, wherein the lipid component coats the Prussian blue nanocube.

11. The method according to claim 8, wherein the lipid component comprises 1,2-dioleoyl-3-trimethylammonium-propane (DOTAP), methoxy-polyethylenealdehyde (mPEG-CHO) and cholesterol.

12. A method for enhancing gene delivery efficiency, comprising administering to a subject in need thereof a composition comprising an effective amount of the carrier according to claim 1.

13. The method according to claim 12, wherein the lipid component coats the Prussian blue nanocube.

14. A method for gene therapy of cancer, comprising administering to a subject in need thereof a pharmaceutical composition comprising an effective amount of the carrier according to claim 1.

15. The method according to claim 14, wherein the cancer is lung cancer.

16. The method according to claim 14, wherein the lipid component coats the Prussian blue nanocube.

17. A method for targeting lung, comprising administering to a subject in need thereof a composition comprising an effective amount of the carrier according to claim 1.

18. The method according to claim 17, wherein the lipid component coats the Prussian blue nanocube.

* * * * *